(12) United States Patent
Cadieux et al.

(10) Patent No.: US 9,963,260 B2
(45) Date of Patent: May 8, 2018

(54) ROTATABLE DRUM AND METHOD AND SYSTEM USING THE SAME FOR THE AUTOMATED PRODUCTION OF E-VAPOR DEVICES

(71) Applicants: Edmond J. Cadieux, Mechanicsville, VA (US); Martin Garthaffner, Chesterfield, VA (US); Barry S. Smith, Richmond, VA (US)

(72) Inventors: Edmond J. Cadieux, Mechanicsville, VA (US); Martin Garthaffner, Chesterfield, VA (US); Barry S. Smith, Richmond, VA (US)

(73) Assignee: Altria Client Services LLC, Richmond, VA (US)

( * ) Notice: Subject to any disclaimer, the term of this patent is extended or adjusted under 35 U.S.C. 154(b) by 295 days.

(21) Appl. No.: 14/686,519

(22) Filed: Apr. 14, 2015

(65) Prior Publication Data
US 2015/0291301 A1    Oct. 15, 2015

Related U.S. Application Data

(60) Provisional application No. 61/979,330, filed on Apr. 14, 2014.

(51) Int. Cl.
*B65C 9/00* (2006.01)
*B65C 9/02* (2006.01)
(Continued)

(52) U.S. Cl.
CPC ............. *B65C 9/02* (2013.01); *A24C 5/327* (2013.01); *A24F 47/008* (2013.01); *B65C 9/08* (2013.01);
(Continued)

(58) Field of Classification Search
CPC .... B65C 3/02; B65C 3/04; B65C 9/02; B65C 9/1865; B65C 9/26; A24F 47/002;
(Continued)

(56) References Cited

U.S. PATENT DOCUMENTS 3,811,567 A    5/1974 Tomita et al.
3,837,378 A    9/1974 Kanki et al.
(Continued)

FOREIGN PATENT DOCUMENTS

CN    101310632 A    11/2008
CN    201758770 U    3/2011
(Continued)

OTHER PUBLICATIONS

International Preliminary Report on Patentability issued in International Application No. PCT/US2015/025754, dated Oct. 27, 2016.
(Continued)

*Primary Examiner* — Carson Gross
(74) *Attorney, Agent, or Firm* — Harness, Dickey & Pierce, P.L.C.

(57) ABSTRACT

A rotating drum for use in manufacturing vapor-generating articles may include a drum body. A plurality of grooves may be disposed in an outer face of the drum body. A seat may be tractably-mounted in each one of the plurality of grooves. The seat may include a seat groove that is structured and arranged to receive and hold a rigid casing of a vapor-generating article. The seat may be composed of a material that is softer than a material of the rigid casing.

19 Claims, 10 Drawing Sheets

(51) Int. Cl.
    *B65C 9/08*     (2006.01)
    *B65C 9/26*     (2006.01)
    *B65G 47/86*     (2006.01)
    *A24F 47/00*     (2006.01)
    *A24C 5/32*     (2006.01)
    *A61M 15/06*     (2006.01)
    *B65C 3/08*     (2006.01)
    *B65C 3/06*     (2006.01)

(52) U.S. Cl.
    CPC .............. *B65C 9/26* (2013.01); *B65G 47/847* (2013.01); *A61M 15/06* (2013.01); *B65C 3/06* (2013.01); *B65C 3/08* (2013.01)

(58) Field of Classification Search
    CPC .... A24F 47/004; A24F 47/006; A24F 47/008; A24C 5/327; A24C 5/56; A24C 5/58; A24C 5/586; A61M 15/06
    See application file for complete search history.

(56) References Cited

U.S. PATENT DOCUMENTS

| | | | |
|---|---|---|---|
| 3,986,320 A | 10/1976 | Bausch et al. | |
| 4,980,969 A | 1/1991 | Marchesini et al. | |
| 5,024,242 A * | 6/1991 | Garthaffner | A24C 5/00 131/280 |
| 5,116,298 A | 5/1992 | Bondanelli et al. | |
| 5,390,469 A | 2/1995 | Shimizu et al. | |
| 5,464,495 A | 11/1995 | Eder | |
| 7,296,578 B2 * | 11/2007 | Read, Jr. | A24C 5/601 131/106 |
| 2002/0005207 A1 | 1/2002 | Wrenn et al. | |
| 2004/0020500 A1 | 2/2004 | Wrenn et al. | |
| 2005/0217207 A1 | 10/2005 | Konishi et al. | |
| 2008/0017203 A1 | 1/2008 | Fagg et al. | |
| 2012/0167906 A1 | 7/2012 | Gysland | |
| 2013/0199550 A1 * | 8/2013 | Ono | A24C 5/472 131/280 |
| 2014/0041655 A1 * | 2/2014 | Barron | A61M 11/042 128/202.21 |
| 2015/0272204 A1 | 10/2015 | Kraisuwannasarn | |
| 2017/0006921 A1 | 1/2017 | Lemay et al. | |

FOREIGN PATENT DOCUMENTS

| | | |
|---|---|---|
| CN | 103491812 A | 1/2014 |
| DE | 1532561 A1 | 4/1970 |
| DE | 3117999 A1 | 11/1982 |
| EP | 0330495 A2 | 8/1989 |
| EP | 0544089 A2 | 6/1993 |
| JP | 2005247325 A | 9/2005 |
| WO | WO-2013002657 A1 | 1/2013 |
| WO | WO-2013076750 A1 | 5/2013 |
| WO | WO-2015/123558 A2 | 8/2015 |

OTHER PUBLICATIONS

International Preliminary Report on Patentability issued in International Application No. PCT/IB2015/001477, dated Oct. 27, 2016.
"E cigarette labeling machine" uploaded by Cherry Wang, Sep. 1, 2014 [retrieved on Feb. 1, 2016]; Retrieved from the Internet: <URL:https://www.youtube.com/watch?v=7uFodYd0xTI>, times 0:00s to 0:30s.
"Labeling machine auto labeler equipment for Electronic cigarette" uploaded by Penglai Industrial Corporation Limited, Sep. 17, 2013 [retrieved Feb. 1, 2016]: Retrieved from the Internet: <URL:https://www.youtube.com/watch?v=zKyXiOYS8_Y>. time 0:00s to 1:10s.
International Search Report dated Feb. 26, 2016, issued in corresponding International Application No. PCT/US2015/066290.
Written Opinion of the International Searching Authority dated Feb. 26, 2016, issued in corresponding International Application No. PCT/US2015/066290.
International Preliminary Report and Written Opinion of the International Searching Authority dated Apr. 27, 2017, issued in corresponding International Application No. PCT/US2015/055667.
International Search Report dated Feb. 3, 2016, issued in corresponding International Application No. PCT/IB2015/001477.
Written Opinion of the International Searching Authority dated Feb. 3, 2016, issued in corresponding International Application No. PCT/IB2015/001477.
Non-Final Office Action dated Aug. 2, 2017 in copending U.S. Appl. No. 14/883,980.
Third Party Observation issued in European Application No. 15791025.8 dated Aug. 18, 2017.
Ampoule, from Wikipedia, the free encyclopedia, retrieved from https://en.wikipedia.org/w/index.php?title=Ampoule&oldid=784220607, page last edited Jun. 7, 2017.
Vial, from Wikipedia, the free encyclopedia, retrieved from https://en.wikipedia.org/w/index.php?title=Vial&oldid=771730942, page last edited Mar. 23, 2017.
Chinese Office Action dated Aug. 30, 2017 for corresponding Chinese Patent Application No. 201580031588.
International Preliminary Report on Patentability issued in International Application No. PCT/US2015/066290, dated Jun. 20, 2017.
International Search Report dated Feb. 5, 2016, issued in corresponding International Application No. PCT/US2015/055667.
Written Opinion of the International Searching Authority dated Feb. 5, 2016, issued in corresponding International Application No. PCT/US2015/055667.
Office Action for corresponding U.S. Appl. No. 14/686,431 dated Nov. 1, 2017.
Search Report for corresponding European App. No. 15791025.8 dated Nov. 2, 2017.
Third Party observations for corresponding European App. No. 15791025.8 dated Oct. 27, 2017.

* cited by examiner

ROTATABLE DRUM AND METHOD AND SYSTEM USING THE SAME FOR THE AUTOMATED PRODUCTION OF E-VAPOR DEVICES

CROSS-REFERENCE TO RELATED APPLICATION

This application claims priority under 35 U.S.C. § 119(e) to U.S. Provisional Application No. 61/979,330, filed Apr. 14, 2014, the entire contents of which is incorporated herein by reference.

BACKGROUND

Field

This disclosure relates generally to systems and methods for manufacturing vapor-generating articles and, more particularly, to systems and methods for manufacturing electronic vapor devices.

Description of the Related Art

Conventionally, electronic vapor-generating articles are manufactured via a number of manual operations. However, such operations are not only labor intensive and time consuming but also more prone to inconsistency.

SUMMARY

Some example embodiments described herein are directed to automated processes for use in the manufacture of electronic vapor-generating articles, including electronic vapor devices. Some example embodiments are directed to using rotating drums to carry partially complete electronic vapor devices during the assembly operations associated with the manufacture of electronic vapor devices, and to using rotating drums to move the partially complete electronic vapor devices between the assembly operations at workstations in an automated fashion. Some example embodiments are directed to a soft drum for use in manufacturing electronic vapor devices. The soft drum may include a rotating drum having a cylindrical drum surface with resilient contact surfaces to hold electronic vapor devices. The soft drum may be used to hold electronic vapor devices during various assembly operations and may also be used in drum-to-drum transfer of components or finished devices in an automated system for manufacturing the electronic vapor devices. Some example embodiments described herein are directed to automated manufacturing of electronic vapor-generating articles, such as electronic vapor devices, articles, apparatuses, instruments, and other forms regardless of their size and shape.

In accordance with example embodiments disclosed herein, there is a rotating drum for use in manufacturing vapor-generating articles. In an example embodiment, a rotatable drum for automated manufacturing of e-vapor devices may include a drum body including a roll face bounded by opposing end faces, the roll face defining a plurality of pockets therein; and a first seat structure tractably-mounted in each of the plurality of pockets of the drum body, the first seat structure including a first outer surface and an opposing first inner surface, the first outer surface defining a first groove therein and facing outward from the drum body, the first groove configured to receive and hold a first casing of the e-vapor devices, the first seat structure including a material that is more structurally yielding than a material of the first casing of the e-vapor devices.

According to another example embodiment, the rotating drum may include a drum body; a plurality of grooves in an outer face of the drum body; and a respective seat in each one of the plurality of grooves. The seat includes a seat groove that is structured and arranged to receive and hold a rigid casing of a vapor-generating article. The seat is composed of a material that is softer than a material of the rigid casing.

According to another example embodiment, there is a system used in manufacturing vapor-generating articles. The system includes a drum including a drum body, a plurality of grooves in an outer face of the drum body, and a respective seat in each one of the plurality of grooves, wherein each said seat includes a seat groove that is structured and arranged to receive and hold a casing of a vapor-generating article. The system also includes a tagging system that is structured and arranged to attach a label to a respective said casing held in a respective said seat. The system additionally includes a wrapping system that is structured and arranged to wrap the label around the respective said casing.

According to another example embodiment, there is a method of manufacturing vapor-generating articles. The method may include receiving and holding a casing of a vapor-generating article in a seat in a groove of a rotating drum; tagging a label to the casing while the casing is held in the seat; and wrapping the label around the casing.

BRIEF DESCRIPTION OF THE DRAWINGS

Various aspects are further described in the detailed description which follows, in reference to the noted plurality of drawings by way of non-limiting examples of embodiments, in which like reference numerals represent similar parts throughout the several views of the drawings.

DETAILED DESCRIPTION

Figure 1A:
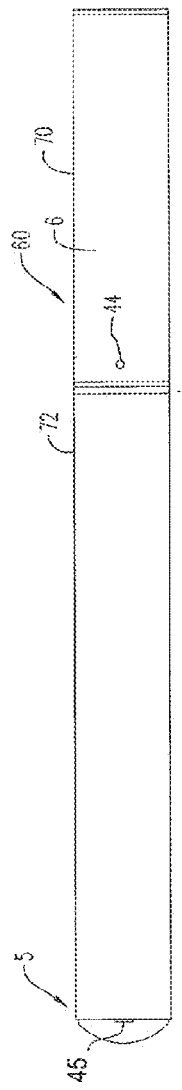
FIGS. 1a, 1b, 1c, and 1d show electronic vapor devices in accordance with an example embodiment.

Various aspects will now be described with reference to specific forms selected for purposes of illustration. It will be appreciated that the spirit and scope of the apparatus, system and methods disclosed herein are not limited to the selected forms. Moreover, it is to be noted that the figures provided herein are not drawn to any particular proportion or scale, and that many variations can be made to the illustrated forms. Reference is now made to FIGS. 1-9, wherein like numerals are used to designate like elements throughout.

Each of the following terms written in singular grammatical form: "a," "an," and "the," as used herein, may also refer to, and encompass, a plurality of the stated entity or object, unless otherwise specifically defined or stated herein, or, unless the context clearly dictates otherwise. For example, the phrases "a device," "an assembly," "a mechanism," "a component," and "an element," as used herein, may also refer to, and encompass, a plurality of devices, a plurality of assemblies, a plurality of mechanisms, a plurality of components, and a plurality of elements, respectively.

Each of the following terms: "includes," "including," "has," "having," "comprises," and "comprising," and, their linguistic or grammatical variants, derivatives, and/or conjugates, as used herein, means "including, but not limited to."

Throughout the illustrative description, the examples, and the appended claims, a numerical value of a parameter, feature, object, or dimension, may be stated or described in terms of a numerical range format. It is to be fully understood that the stated numerical range format is provided for illustrating implementation of the forms disclosed herein, and is not to be understood or construed as inflexibly limiting the scope of the forms disclosed herein.

Moreover, for stating or describing a numerical range, the phrase "in a range of between about a first numerical value and about a second numerical value," is considered equivalent to, and means the same as, the phrase "in a range of from about a first numerical value to about a second numerical value," and, thus, the two equivalently meaning phrases may be used interchangeably.

It is to be understood that the various forms disclosed herein are not limited in their application to the details of the order or sequence, and number, of steps or procedures, and sub-steps or sub-procedures, of operation or implementation of forms of the method or to the details of type, composition, construction, arrangement, order and number of the system, system sub-units, devices, assemblies, sub-assemblies, mechanisms, structures, components, elements, and configurations, and, peripheral equipment, utilities, accessories, and materials of forms of the system, set forth in the following illustrative description, accompanying drawings, and examples, unless otherwise specifically stated herein. The apparatus, systems and methods disclosed herein can be practiced or implemented according to various other alternative forms and in various other alternative ways.

It is also to be understood that all technical and scientific words, terms, and/or phrases, used herein throughout the present disclosure have either the identical or similar meaning as commonly understood by one of ordinary skill in the art, unless otherwise specifically defined or stated herein. Phraseology, terminology, and, notation, employed herein throughout the present disclosure are for the purpose of description and should not be regarded as limiting.

Aspects described herein are directed to a soft drum for use in manufacturing electronic vapor devices. Although example embodiments are described with reference to electronic vapor devices, it is understood that aspects described herein may be used with similar devices, articles, apparatuses, instruments, and utensils. The soft drum described herein may include a resilient cylindrical drum surface with grooves to hold electronic vapor devices securely and to transfer the devices among various assembly operations. In example embodiments, the resiliency of the drum surface is provided by at least one of a surface material of the drum being relatively softer than a surface material of the electronic vapor device; and a portion of the drum being moveable in an axial direction of the drum. In this manner, example embodiments are useful for carrying and transferring electronic vapor devices during manufacturing operations.

Electronic Vapor Device Layout

Figure 1B:
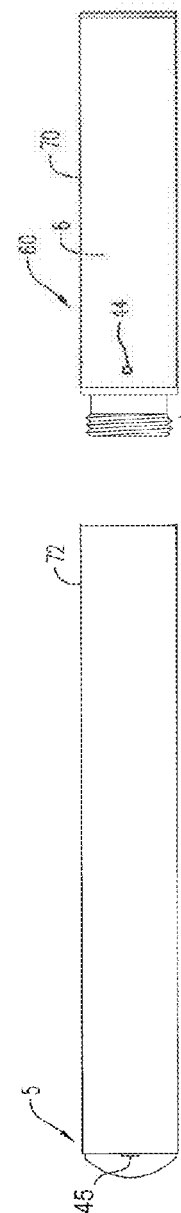
Figure 1C:
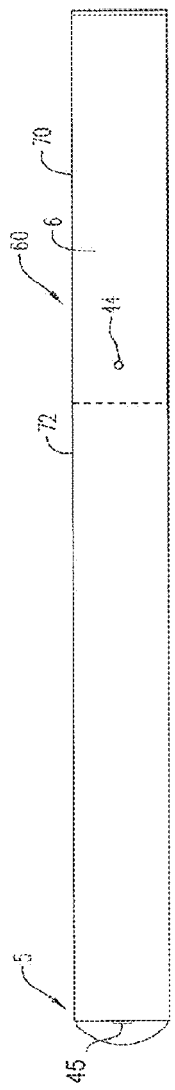
Figure 1D:
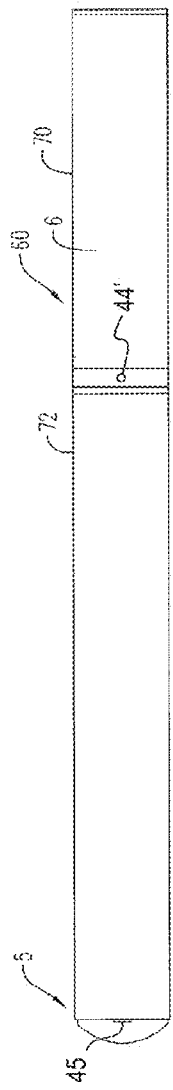

Referring to FIGS. 1a and 1b, an electronic vapor device (article) 60 is provided and comprises a replaceable cartridge (or first section) 70 and a reusable fixture (or second section) 72, which are coupled together at a threaded connection 205 or by other convenience such as a snug-fit, detent, clamp, and/or clasp. Generally, the second section 72 includes a puff sensor responsive to air drawn into the second section 72 via an air inlet port 45 adjacent the free end or tip of the electronic vapor device 60, a battery, and control circuitry. The disposable first section 70 includes a liquid supply region and a heater that vaporizes liquid that is drawn from the liquid supply region through a wick. In an example embodiment, the first section 70 is a cartomizer section and includes an outer casing 6 that houses the liquid supply region, heater, and wick. Upon completing the threaded connection 205, the battery of the second section 72 is connectable with the electrical heater of the first section 70 upon actuation of the puff sensor. Air is drawn primarily into the first section 70 through one or more air inlets 44 during drawing action upon the mouth end of the first section 70. The drawing action is communicated to a puff sensor in the second section 72 which causes the battery-powered heater to vaporize some of the liquid from the liquid supply region. The vaporized liquid is entrained in the air that is drawn in through the one or more air inlets 44 and delivered to the mouth of the user via one or more ports at the mouth end of the first section 70. As shown in FIG. 1d, the one or more air inlets 44' may be located at a structure associated with the threaded connection 205, including but not limited to a connector ring between the first section 70 and the second section 72.

In an example embodiment, once the liquid of the cartridge is spent, only the first section 70 is replaced. An alternate arrangement shown in FIG. 1c includes an implementation in which the first section 70 and the second section 72 are integrally attached, such that the entire article 60 is disposed once the liquid supply is depleted. In such case, the battery type and other features might be engineered for simplicity and cost-effectiveness, but generally embodies the same concepts as in an example embodiment in which the second section is reused and/or recharged.

In an example embodiment, the electronic vapor device 60 may be about 80 mm to about 110 mm long (e.g., about 80 mm to about 100 mm long) and about 7 mm to about 10 mm or more in diameter. For example, the electronic vapor device is about 84 mm long and has a diameter of about 7.8 mm. Implementations are not limited to these dimensions, and aspects described herein may be adapted for use with any size electronic vaping article.

At least one adhesive-backed label may be applied to the outer casing 6 of the first section 70. The label completely circumscribes the electronic vapor device 60 and can be colored and/or textured. The label can include holes therein which are sized and positioned so as to prevent blocking of the air inlets 44.

The outer casing 6 may be formed of any suitable material or combination of materials. Examples of suitable materials include metals, alloys, plastics, paper, fiberglass (including woven fiberglass) or composite materials containing one or more of those materials, or thermoplastics that are suitable for food or pharmaceutical applications, for example polypropylene, polyetheretherketone (PEEK), ceramic, and polyethylene. The material may be light and non-brittle. In an example implementation, the outer casing 6 is composed of metal (e.g., aluminum or aluminum alloy).

Automated Manufacture Using Rotating Drums

FIGS. 2a-2d and 3 show aspects of systems and methods for the automated manufacture of vapor-generating articles (such as, by way of example, electronic vapor devices) using rotating drums in accordance herewith. Aspects of FIGS. 2a-2d and 3 are described with respect to automated manufacturing processes associated with the first section 70 (also referred to herein as a cartridge unit 70) of an electronic vapor device 60. The systems and methods described herein are not limited to use with the first section 70, however, and instead may be used with automated manufacturing processes associated with a second section 72 (e.g., a battery section) and/or a combined article including a connected first section 70 and second section 72.

Figure 2A:
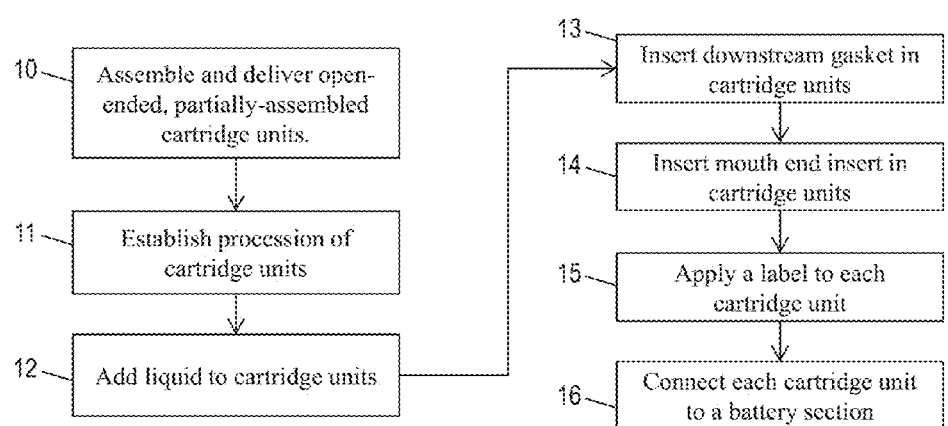
FIG. 2a is a block diagram of a process for automated assembly of electronic vapor devices in accordance with an example embodiment.

FIG. 2a is a block diagram of a process for automated assembly of electronic vapor devices in accordance with an example embodiment. The process may include assembling and delivering open-ended, partially-assembled cartridge units 70 (step 10); establishing a procession of the open-ended, partially-assembled cartridge units 70 (step 11); adding liquid to the liquid supply region of the cartridge units 70 (step 12); inserting a respective downstream gasket into each of the cartridge units 70 (step 13); inserting a respective mouth end insert into each of the cartridge units 70 (step 14); applying a respective label to the outer casing of each of the cartridge units 70 (step 15); and connecting a respective battery section (i.e., second section 72) to each of the cartridge units 70 (step 16). In aspects, the processes performed at steps 11-16 are automated, e.g., using computer-controlled manufacturing machinery. In additional aspects, the cartridge units 70 are handled and transported during and between steps 11-16 in an automated manner, e.g., using rotating drums as described herein. In even further aspects, one or more inspection processes is performed after each one of steps 11-16, e.g., to detect cartridge units 70 that are out of specification. The method is not limited to the particular steps 10-16; instead, more or less steps and/or different steps and/or a different order of steps may be used.

Figure 2B:
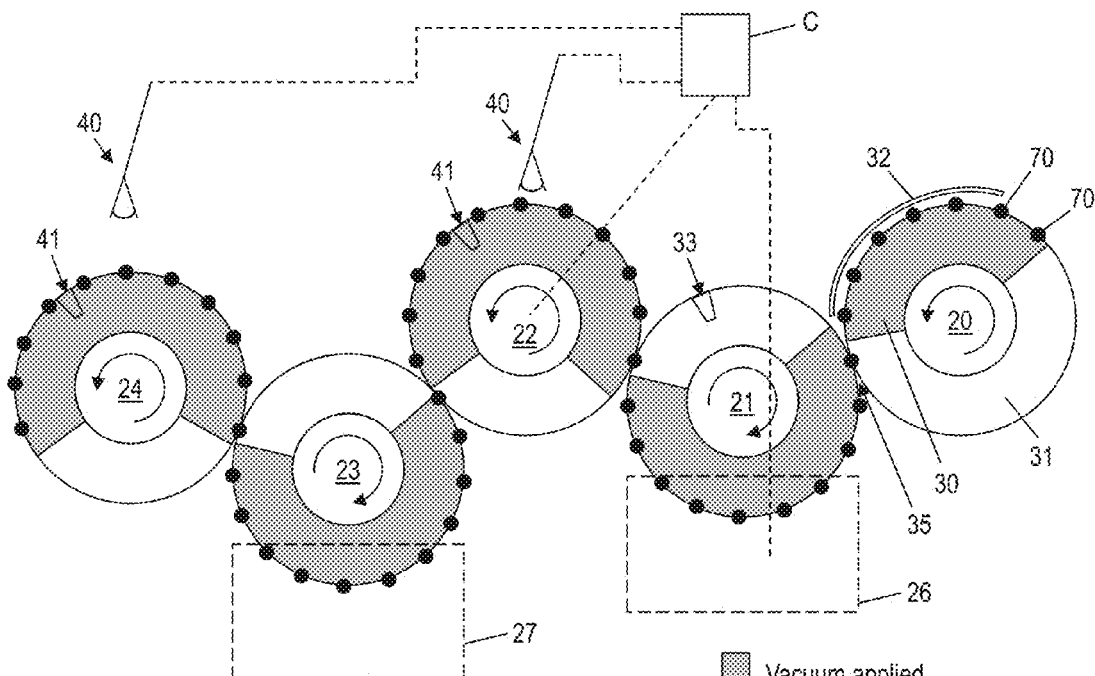
FIGS. 2b-2d show aspects of systems and methods for the automated manufacture of electronic vapor devices using rotating drums in accordance with an example embodiment.
Figure 2C:
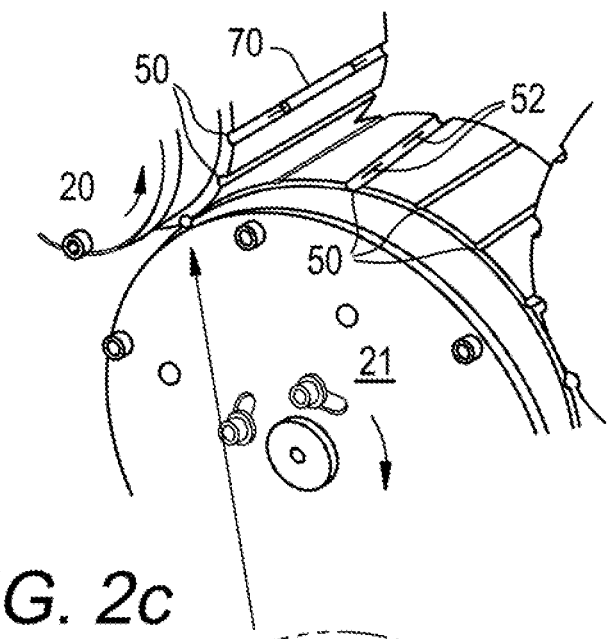
Figure 2D:
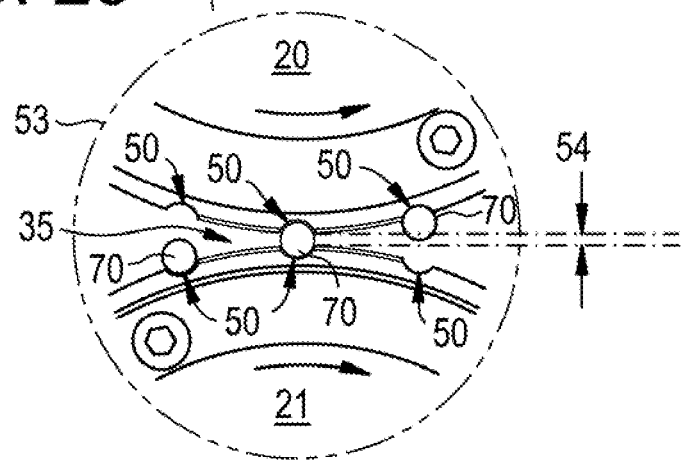
Figure 2D:
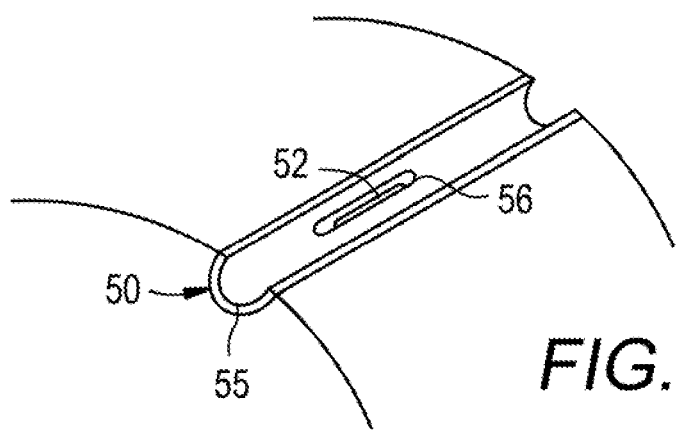

FIGS. 2b-2d depict drum-to-drum transfer systems and methods that may be used with aspects of automated assembly of electronic vapor devices in accordance herewith. Aspects shown in FIGS. 2b-2d may be used in the handling and transporting of cartridge units 70 during and between steps 11-16 described with respect to FIG. 2a, for example. As shown in FIG. 2b, a procession of a plurality of cartridge units 70 (shown individually as solid circles) may be carried by a plurality of rotating drums 20-24 to work stations 26, 27 where manufacturing/assembly processes are performed on the cartridge units 70. In aspects, the work stations 26, 27 may correspond to any of steps 11-16. In but one example, work station 26 may include machinery configured to insert a respective downstream gasket into each of the cartridge units 70, and work station 27 may include machinery configured to insert a respective mouth end insert into each of the cartridge units 70. Although only two work stations 26, 27 are shown for simplicity, it is understood that rotating drums similar to drums 20-24 may be used to carry cartridge units 70 to other work stations during the automated manufacture of electronic vapor devices.

In example embodiments, each drum 20-24 may include a cylindrical body with a plurality of grooves (also called flutes) spaced apart on its roll face. Each flute may be structured and arranged to hold and carry a section of an electronic vapor device, such as a cartridge unit 70. As described in greater detail with respect to FIGS. 2c and 2d, each flute may include a resilient (e.g., yieldable) material that directly contacts the cartridge unit 70 when the cartridge unit 70 is held in the flute and carried by the rotating drum.

Still referring to FIG. 2b, each drum 20-24 may include a vacuum system that selectively applies a vacuum force to the flutes to assist in holding the cartridge units 70 in the flutes during rotation of the drum. For example, the system may be adapted such that during rotation of the drums 20-24, flutes that are located in shaded areas 30 are provided with a vacuum force, while flutes that are located in unshaded areas 31 are not provided with the vacuum force. Specifically, a particular flute on counterclockwise rotating drum 20 is provided with the vacuum force when the flute is moving through the shaded area 30, and is not provided with the vacuum force when the flute is moving through the unshaded area 31. The vacuum force may be selectively applied to each flute on each drum individually, such as via a vacuum port in each flute and a vacuum source internal to the drum that selectively applies a vacuum force to the vacuum port in a particular flute based on the angular position of the particular flute along the rotational path of the roll face of the drum.

Rails 32 may also be provided adjacent to one or more of the drums 20-24 to assist in maintaining the cartridge units 70 in the flutes. Further, cleaning air may be communicated to the port(s) of each flute at angular positions such as that indicated by area 33. The cleaning air may be selectively applied to each flute individually.

In aspects, when transferring a cartridge unit 70 from a donating flute of a first drum to a receiving flute of a second drum, e.g., from drum 20 to drum 21, a vacuum force is deactivated at the donating flute when the donating flute is at a location prior to the nip 35 between the first drum and the second drum. Also, a vacuum force is activated at the receiving flute when the receiving flute is at a location prior to the nip 35 between the first drum and the second drum. This coordination of the timing of the respective vacuum forces applied at the donating flute and the receiving flute is depicted by shaded areas 30 and unshaded areas 31 in FIG. 2b and facilitates moving the cartridge unit 70 out of the donating flute and into the receiving flute.

With continued reference to FIG. 2b, the system may include a controller "C" that is operatively connected to one or more elements. As described herein, the controller "C" may be a computer-based controller that employs hardware and software to perform automated control processes. For example, the controller "C" may be operatively connected to one or more detectors 40 for the purpose of inspecting and/or tracking cartridge units 70 during the automated manufacturing. The detectors 40 may comprise cameras or other optical detecting mechanisms that detect optical characteristics and/or information of the cartridge units 70 and transmit the detected optical characteristics and/or information to the controller "C".

For inspection purposes, the controller "C" may determine whether a cartridge unit 70 is out of specification, e.g., not properly assembled, damaged, etc., by comparing the detected optical characteristics to predefined optical criteria. Any cartridge unit 70 that is determined to be out of specification based on the detecting may be ejected from one of the rotating drums, e.g., by selectively disabling the vacuum of a flute carrying the out of specification cartridge unit and/or applying a jet of air to the flute, e.g., as indicated at location 41, to eject the cartridge unit 70 from the flute. It is envisioned that an inspection station may be located downstream of the ejection station 41, to confirm proper operation of the ejection station 41. The controller "C" may be programmed to track any empty flute position resulting from an ejection, and to track the empty flute position through the system (e.g., the entire system or to the next downstream workstation).

Alternatively or in addition, for tracking purposes, each cartridge unit 70 may be encoded with information such as: date of manufacture, unique tracking identification, authentication, lot number, facility identification, and model number. More specifically, the individual cartridge units 70 may be printed with indicia that provide such information. The detectors 40 may include a device, such as a camera or bar code reader, which reads the encoded information on each of the cartridge units as the cartridge units are moved by the drums 20-24. The controller "C" may be programmed to track the position of each cartridge unit 70 in the system based on the encoded information detected by the detectors 40.

As depicted in FIG. 2b, the controller "C" may also be operatively connected to the drums 20-24, for example, to control the rotational speed of each drum. The controller "C" may also be operatively connected to the work stations 26, 27, for example, to control aspects of the automated processes that are performed at the stations.

FIGS. 2c and 2d show example aspects of the flutes and drums as described herein. In example embodiments, the flutes 50 that receive and carry the cartridge units 70 are embodied as grooves or channels at the outer surface (e.g., roll face) of the rotating drums (e.g., drums 20-24). As shown in FIG. 2c, in aspects herein, the longitudinal axis of the cartridge unit 70 is transverse to the direction of rotation of the drum when the cartridge unit 70 is seated in the flute 50. Each flute 50 may include at least one port 52 that is in communication with a vacuum/pressure source of the drum. Depending on the angular location of the flute 50 along the rotational path of the drum, the vacuum/pressure source of the drum may selectively apply a vacuum, an air jet, or no force at the port 52, e.g., as described with respect to areas 30, 31, and 33 of FIG. 2b.

As shown in the magnified portion 53 of FIG. 2c, there is a clearance 54 between the roll surfaces of the respective drums (e.g., drums 20 and 21) at the nip 35 between the drums. For example, when the cartridge unit 70 has an outside diameter of about 7.8 mm, the clearance 54 may be about 0.5 mm to about 1 mm, although any suitable dimension of clearance may be used.

As shown in FIG. 2d, the surface of each flute 50 may be coated or covered with a resilient (e.g., yieldable) material 55. An opening 56 in the resilient material 55 aligns with the port 52 such that vacuum or an air jet may be applied to the flute via the port 52 and opening 56. The resilient material 55 may be applied to surfaces of the drum outside of the flutes 50, for example, over the entire roll face of the drum. In another embodiment, the entire drum (e.g., drums 20-24) may be constructed of the resilient material 55. In another embodiment, the resilient material 55 is provided over less than the entire flute 50; for example, a seat of resilient material may be provided in a sub-section of a flute (e.g., as described with respect to FIGS. 4-8). Such a resilient material 55 may be used with any type of drum based on the system requirements, including but not limited to a wrapping drum, MR drum, roll hand, etc.

In accordance with aspects herein, the resilient material 55 comprises a material that is softer (i.e., has a lower hardness) than the material of the outer casing 6 of the cartridge unit 70. For example, the outer casing 6 may be composed of a metal or metal alloy and the resilient material 55 may be composed of a plastic or rubber material. The outer casing 6 may be composed of an aluminum alloy and the resilient material 55 may be composed of polyoxymethylene (POM, Delrin, etc.), although embodiments are not limited to these materials and any suitable materials may be used.

The resilient material 55 facilitates handling the cartridge units 70 during the speeds that are involved with the rotating drums during the automated manufacture of electronic vapor devices 60 as described herein. In particular, the yieldable nature of the resilient material 55 promotes a more complete seal of the cartridge unit 70 at the vacuum port in a flute, which enhances the vacuum retention force applied to the cartridge unit 70 in the flute. Such arrangement assures retention of articles on the flutes even at higher production speeds and/or with heavier, larger articles.

The cartridge unit 70 of an electronic vapor device 60 as described herein is more rigid and heavier than components of similar conventional articles. As a result, the metal flutes that are typically used in rotating drums in the production of conventional articles are ill-suited for handling the cartridge unit 70. For example, conventional articles that are lightweight and constructed of paper may experience slight, temporary deformation inside a metal flute of a rotating drum. This deformation causes the conventional article to cover the entire vacuum port, which leads to a suitable retention force for holding the article in the flute. On the other hand, the cartridge unit 70, owing to its increased rigidity and weight, experiences much less deformation or no deformation at all in the flute of a rotating drum. Therefore, according to aspects herein, the surface of the flute is provided with the resilient material 55 that yields under the force of the cartridge unit 70. The yielding nature of the resilient material 55 permits the cartridge unit 70 to press into the resilient material 55 and more completely cover the opening 56 and vacuum port 52, which provides a greater vacuum retention force on the cartridge unit 70 compared to the situation where a resilient material is not used.

Figure 3:
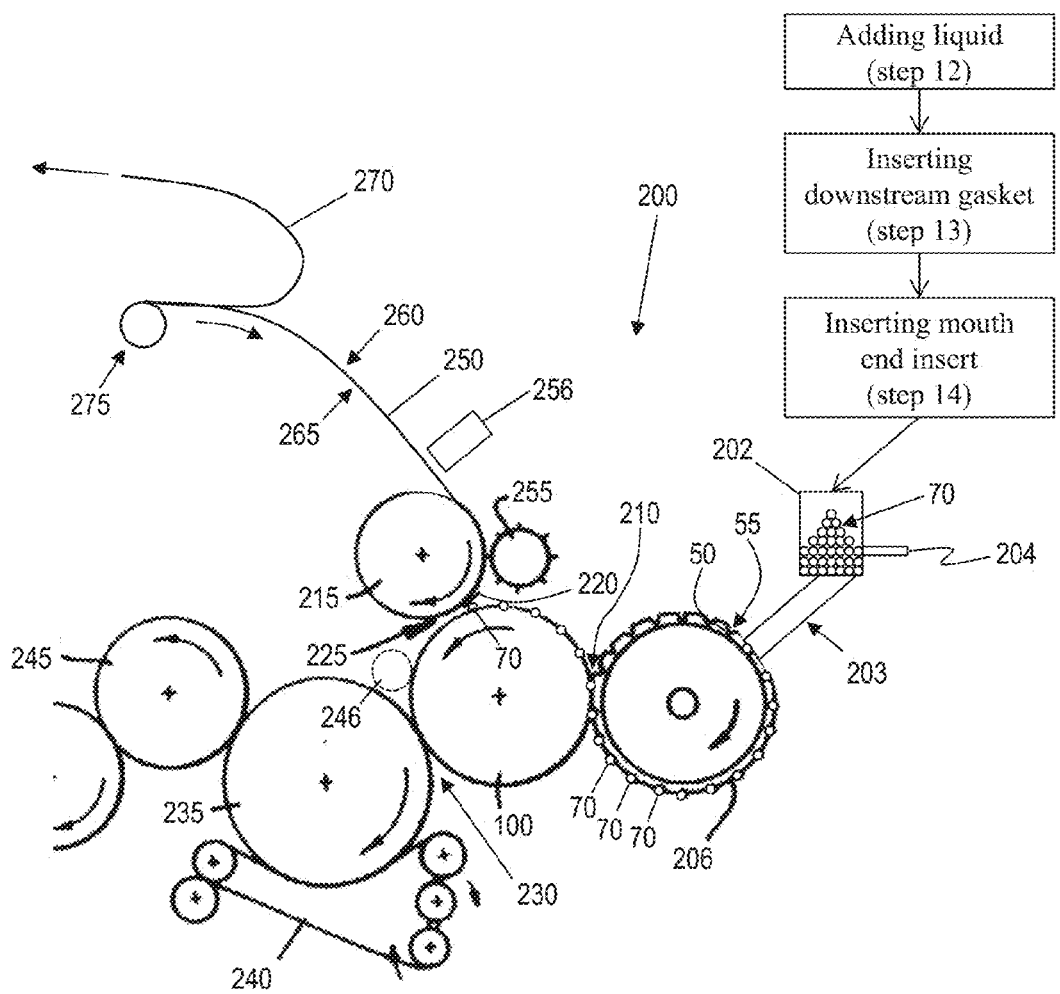
FIG. 3 shows aspects of an automated system for applying a label to an electronic vapor device in accordance with an example embodiment.

FIG. 3 shows aspects of a system 200 for the automated applying of labels to electronic vapor devices in accordance with an example embodiment. The system 200 may be, for example, part of a tipping machine utilized in the manufacture of electronic vapor device 60. As described herein, a label or wrapper may be applied to the exterior surface of the casing 6 of the first section (i.e., cartridge unit) 70 to provide a desired aesthetic appearance and/or tactile feel to the electronic vapor device 60. The system 200 may be part of an automated assembly path as disclosed in U.S. application Ser. No. 14/686,431, filed concurrently herewith, the entire contents of which are expressly incorporated herein by reference. The system may include aspects of machinery described in U.S. Pat. No. 5,024,242, the entire contents of which are expressly incorporated herein by reference.

In example embodiments, the system 200 may be used to perform step 15 as described with respect to FIG. 2a. In such an implementation, the system 200 may include an accumulator 202 that receives and holds a plurality of cartridge units 70 after they have undergone processing of steps 12-14 as described with respect to FIG. 2a. The accumulator 202 functions as a buffer between the machinery that performs step 14 and that of step 15. The accumulator 202 may comprise, for example, a zig-zag or S-shaped pathway through which the cartridge units 70 travel between an accumulator inlet and an accumulator outlet 203. The accumulator inlet may be vertically higher than the accumulator outlet 203 such that the cartridge units 70 travel through the accumulator via gravity. The accumulator 202 may be sized to receive cartridge units at the accumulator inlet at a faster rate than cartridge units are released at the accumulator outlet 203. In this manner, the accumulator 202 provides a buffer that compensates for empty slots in the procession, e.g., cartridge units that were ejected from the procession based on the inspection step or missing in the procession as a result of inconsistent loading. A sensor 204, such as a photo eye or similar, may be arranged at the accumulator 202 to determine whether the amount of cartridge units 70 in the accumulator 202 exceeds a threshold. The sensor 204 may be operatively connected to a controller of the system 200. When the sensor 204 communicates to the controller that the level of cartridge units 70 in the accumulator 202 falls below the threshold, the controller may temporarily stop the drums downstream of the accumulator 202, i.e., to pause the labeling operation. This pausing permits cartridge units 70 to accumulate in the accumulator 202 since the upstream equipment may continue to process and deliver cartridge units 70 to the accumulator 202. The sensor 204 detects when a sufficient number of cartridge units 70 has accumulated in the accumulator 202 (i.e., exceeds the threshold), at which time the controller, based on the signal from the sensor 204, automatically re-starts the drums of system 200 to resume the labeling operation.

In example embodiments, a transfer drum 206 with flutes 50 around its outer perimeter receives cartridge units 70 from the accumulator outlet 203. The transfer drum 206 may be similar to the drums 20-24 described with respect to FIG. 2b. For example, each flute 50 of the transfer drum 206 is sized to receive a single cartridge unit 70. Each flute may also be provided with a resilient material 55 for contacting the cartridge unit 70. Each flute 50 may also have at least one aperture (such as port 52 and opening 56) that is configured to selectively communicate a vacuum force to a cartridge unit seated in the flute 50, i.e., for keeping the cartridge unit 70 seated in the flute 50.

In example embodiments, the system is arranged such that rotation of the drum 206 moves an empty flute 50 past and under the accumulator outlet 203. Gravity pulls a cartridge unit 70 at the accumulator outlet 203 into the empty flute 50. In addition to or alternatively to gravity, air pressure and/or a positive force applied by a wheel or belt may be used to move the cartridge unit 70 at the accumulator outlet 203 into the empty flute 50. Vacuum may also be selectively applied to the flute 50 to assist in pulling the cartridge unit 70 from the accumulator outlet 203 into the empty flute 50. As the drum 206 continues to rotate, the trailing wall of the flute 50 strips the cartridge unit 70 from the accumulator outlet 203. Vacuum may be selectively applied to the flute 50 to maintain the cartridge unit 70 in the flute 50 until rotation of the drum 206 brings the cartridge unit to the next rotating drum 100.

At location 210, the cartridge units 70 are transferred from the transfer drum 206 to a drum 100, which rotates in a direction opposite the rotation of the drum 206. Each cartridge unit 70 is held in a respective seat 115 on the drum 100 as described in greater detail herein with respect to FIGS. 4 and 5. A tagging drum 215 is situated adjacent drum 100 and rotates in a clockwise direction. In example embodiments, the tagging drum 215 carries a plurality of labels 220 and tags a respective label 220 to a respective cartridge unit 70 at location 225.

At location 230, each cartridge unit 70 with its associated label 220 is transferred from the drum 100 to a rolling drum 235, which rotates in a clockwise direction. Rolling drum 235 conveys each cartridge unit 70 and its associated label 220 into contact with belt 240. The belt 240 moves in a same direction as an adjacent portion of the surface of the rolling drum 235 but at a slightly slower speed than the rotation of the rolling drum 235, the speed difference between the belt 240 and the rolling drum 235 causing the cartridge unit 70 to rotate in a direction that causes label 220 to wrap itself around the exterior surface of the cartridge unit 70. After the wrapping operation, the labeled cartridge units 70 are transferred from the rolling drum 235 to a downstream transfer drum 245 for transfer to another station for further processing, e.g., connecting the cartridge unit 70 to a second section 72 (e.g., as described at step 16 of FIG. 2a).

In example embodiments, an additional pressing roller 246 may be provided adjacent to drum 100 at a location after the label is tagged to the cartridge unit 70 and before the cartridge unit 70 is transferred to the rolling drum 235. The pressing roller 246 may be structured and arranged to press an unsecured leading edge 305 (shown in FIG. 7a) of the label 220 to the outer surface of the cartridge unit 70 prior to the cartridge unit 70 being passed to the rolling drum 235.

In further embodiments, the tagging and rolling may be performed on a single drum. For example, a cartridge unit 70 carried in a flute of a drum may be tagged with a label 200 at a first rotational location of the drum, and the label 200 may be rolled around the cartridge unit 70 while the cartridge unit is at a second rotational location of the same drum.

The transfer of the cartridge units 70 from one drum to another in system 200 may be achieved using drum-to-drum transfer techniques described with respect to FIGS. 2b-d. The flutes of one or more of the drums in the system 200 may be provided with a resilient material 55 such as that described with respect to FIGS. 2c-d to facilitate safe and consistent handling of the cartridge units 70 during high-speed rotation of the drums.

As described herein, the tagging drum 215 and the cutter 255 may be part of a tagging system that is structured and arranged to attach a label 220 to a cartridge unit 70 held in seat 115. As described herein, the rolling drum 235 and belt 240 may be part of a wrapping system that is structured and arranged to wrap the label 220 around the cartridge unit 70.

Still referring to FIG. 3, in aspects described herein the label 220 comprises an individual piece of paper or the like that is cut from a continuous web 250. For example, a rotating cutter 255 or the like may cut the continuous web 250 into discrete labels 220 that are held to the surface of tagging drum 215 in a conventional manner by a vacuum. A heater 256, such as a hot air blower, heat plate, radiative element, etc., may be used to heat the web 250 to increase the tackiness of the adhesive prior to tagging.

In example embodiments, a first side 260 of the continuous web 250 has a pressure sensitive adhesive thereon, and a second side 265 of the continuous web 250 has no adhesive. The pressure sensitive adhesive may be pre-applied to the continuous web 250 and covered with a backing sheet 270. For example, the continuous web 250 may be provided by a spool 275 with the adhesive and backing sheet 270 already thereon. The system 200 may be structured and arranged to unwind the continuous web 250 from the spool 275 and then peel the backing sheet 270 from the continuous web 250 to expose the pre-applied adhesive prior to the continuous web 250 coming into contact with the tagging drum 215. The separated backing sheet 270 may be moved away from the continuous web 250 using an air blower or the like. In example embodiments, the spool 275 is fixed to an E-shaft, and the RPM of the E-shaft may be controlled (e.g., selectively varied) to register (e.g., align) a printed logo on a label with a position on the cartridge unit 70 via an eye.

The use of a pre-applied pressure sensitive adhesive (e.g., a peel-and-stick adhesive) on labels 220 provides an advantage over conventional tipping machines that apply an adhesive or a solvent to the tipping paper. In particular, the application of an adhesive or a solvent to the tipping paper requires a transient time at startup of the tipping machine during which some tags are not useable. This leads to waste. The pre-applied pressure sensitive adhesive used in aspects described herein, however, does not require such a transient time during startup, and thus reduces waste when compared to a conventional tipping machine. Implementations as described herein can pause in process of wrapping articles and restart with no loss of product; program stops (e.g., due to upstream equipment) will fully utilize labeling.

Figure 4:
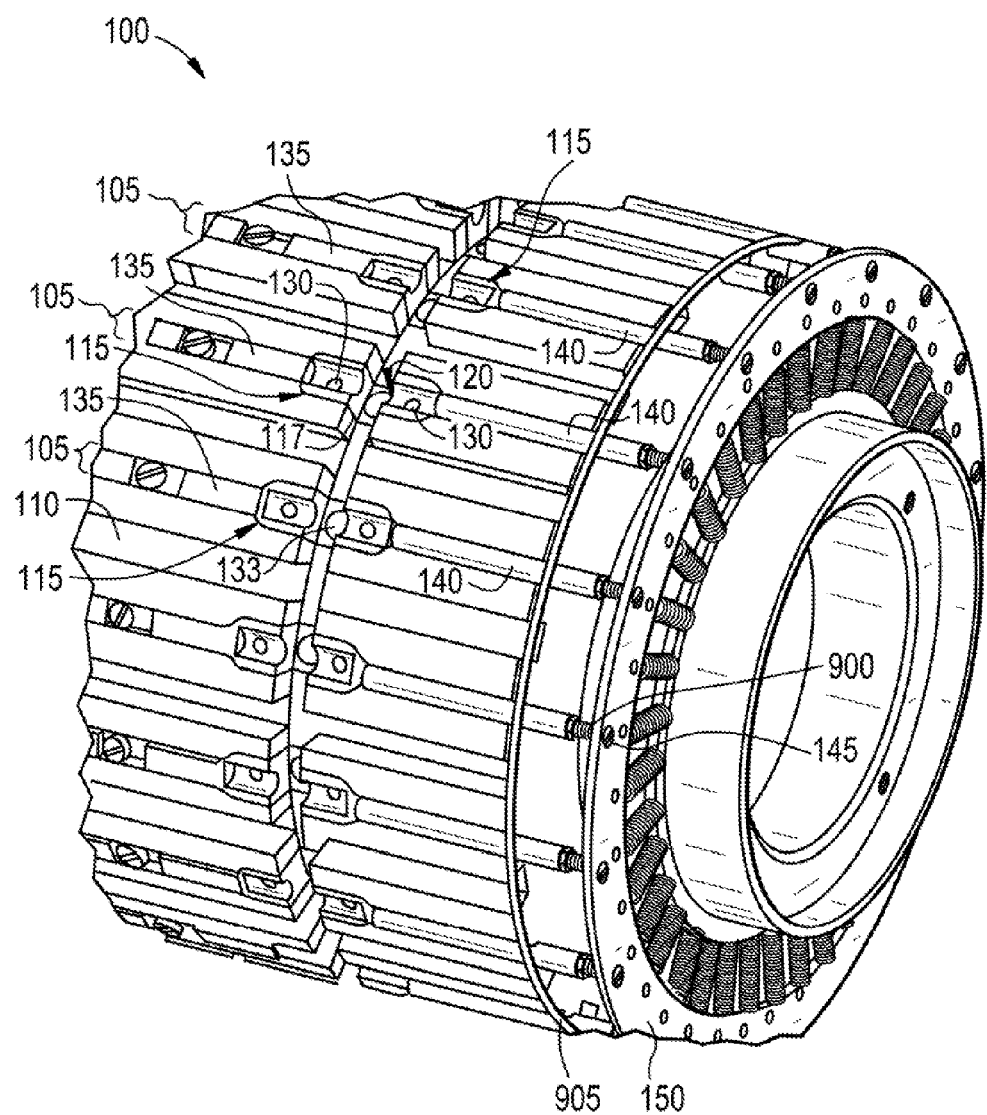
FIGS. 4 and 5 show aspects of a drum in accordance with an example embodiment.
Figure 5:
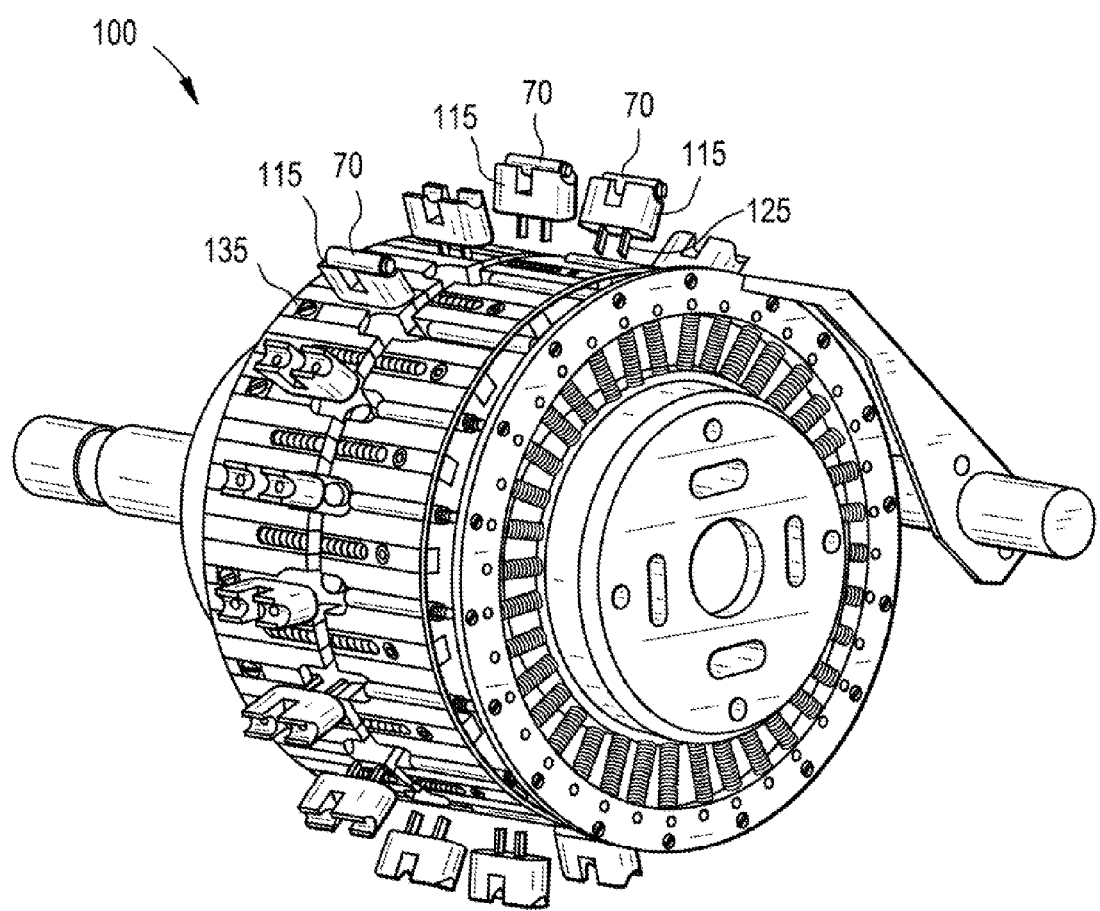

FIGS. 4 and 5 show aspects of a drum 100 in accordance herewith that may be used in manufacturing an electronic vapor device 60 described with respect to FIGS. 1a-b. Drum 100 is described herein with respect to a labeling process during the manufacture of an electronic vapor device. In particular, drum 100 is described herein as a rotational tipping drum that carries a cartridge unit 70 of an electronic vapor device 60 while a label is tagged on the outer casing 6 of the cartridge unit 70. In this regard, the drum 100 may be used as drum 100 in the system of FIG. 3. It is to be understood, however, that drum 100 is not limited to use as a tipping drum, and instead may be used as one or more other drums in an electronic vapor device manufacturing system. Further, it is understood that drum 100 is not limited to use with manufacturing electronic vapor devices, but rather that drum 100 may also be used in manufacturing other articles.

As shown in FIGS. 4 and 5, drum 100 includes a cylindrical body with a plurality of flutes 105 (e.g., pockets, groove, etc.) spaced apart across its roll face 110. The drum 100, including the roll face 110 and the interior surfaces of the flutes 105, may be composed of suitable material, including but not limited to a metal or metal alloy such as steel. In example embodiments, a seat 115 is located in a pocket 117 of each flute 105, and each seat 115 includes a seat groove 120 that is sized and shaped to hold a cartridge unit 70.

In accordance with aspects described herein, a portion of the seat 115 that comes into direct contact with the casing 6 of the cartridge unit 70 is composed of a material that is more structurally yielding (e.g., softer) than the material of the casing 6. For example, as described above, the casing 6 may be composed of metal or metal alloy to facilitate precise machining of the casing 6 and inlet 44. In such embodiments, the seat 115 may be composed of a material that is softer (i.e., has a lower hardness) than the metal or metal alloy material of the casing 6. For example, the casing 6 may be composed of a metal or metal alloy and the seat 115 may be composed of a plastic. The casing 6 may be composed of an aluminum alloy and the seat 115 may be composed of polyoxymethylene (POM, Delrin, etc.). In this manner, the seat 115 may correspond to the resilient material 55 described with respect to FIGS. 2c-d.

FIG. 5 shows an exploded view of a number of seats 115 relative to the drum 100. In aspects described herein, each seat 115 is resiliently biased against the drum 100. For example, as shown in FIGS. 5 and 7, one or more springs 125 are positioned between the bottom of the seat 115 and the drum 100. When the seat 115 is seated in the pocket 117 of a flute 105, the springs 125 resiliently bias the seat 115 in an outward direction along a radial axis of the drum 100. A limit stop structure 133 (see FIG. 7) may be used to limit the outward movement of the seat 115 (e.g., radially outward relative to the drum). The springs 125 permit the seat 115 to be pushed inward along a radial axis of the drum 115 when a sufficient force is applied to the seat 115 that overcomes the spring force of the springs 125. The pocket 117 of the flute 105 may be appropriately sized to accommodate the springs 125 and a predefined amount of inward movement of the seat 115 when the seat 115 is positioned in the pocket 117. Because the seat 115 may include (e.g. covering layer) or be formed of a material that is more structurally yielding than the casing 6 of the cartridge unit 70 and/or be configured to resiliently travel in (e.g., retract) and out (e.g., protract) of a corresponding pocket 117, the seat 115 may be regarded as being "tractably-mounted" in a corresponding pocket 117.

With continued reference to FIGS. 4 and 5, each seat 115 may be provided with one or more holes 130 that are structured and arranged to provide a vacuum to hold a cartridge unit 70 in the seat groove 120. The use of vacuum to hold objects to drums in manufacturing is understood by those of skill in the art, such that further explanation is not necessary. In a particular embodiment shown in FIG. 7a, the hole 130 is aligned with the spring 125, and a tube or similar structure located within the perimeter of the spring 125 provides a vacuum communication path between the vacuum source of the drum and the hole 130 as described in greater detail herein. In another embodiment shown in FIG. 7b, the holes 130 are offset from the springs 125.

Still referring to FIGS. 4 and 5, each seat 115 may be bounded in the flute 105 on one side by a stop 135 and on another side by a pusher 140. The stop 135 may be a structural element that is non-moveably connected to the drum 100 or may be an integral portion of the drum 100. The stop 135 may be a bar or block that sits in a portion of the flute 105 and is affixed to the drum 100 by a threaded connector such as a screw or bolt. In aspects described herein, the pusher 140 is a structural element that is held within the flute 105 and is translatable in the flute 105 along the longitudinal axis of the flute 105. In example embodiments, the pusher 140 is configured to be selectively urged toward the seat 115. In this manner, when a cartridge unit 70 is situated in the seat groove 120 of a seat 115, the pusher 140 may contact the cartridge unit 70 and exert an axial force on the cartridge unit 70 that pushes the cartridge unit 70 against the stop 135. A swash plate 150 or similar mechanism may be structured and arranged to selectively act on the pusher 140 based on the rotational position of the drum in order to selectively apply the axial force to the cartridge unit 70 at certain times during the rotation of drum 100, e.g., during tagging as described herein. In this manner, the cartridge unit 70 may be held steady in the seat 115 during a manufacturing step, such as tagging a label to the casing 6 of the cartridge unit 70.

In example embodiments, the seat 115, the stop 135, the pusher 140, and the swash plate 150 are structured and arranged such that the pusher 140 pushing the cartridge unit 70 against the stop 135 causes the cartridge unit 70 to be aligned with a label that is being applied to (e.g., tagged to) the cartridge unit 70. The stop 135 is at a known location on the drum, such that pushing the cartridge unit 70 against the stop 135 places the cartridge unit 70 at a known location. In this manner, pushing the cartridge unit 70 against the stop 130 is used to repeatedly and consistently place each cartridge unit 70 in a known location at the time of tagging. For example, the swash plate 150 may be configured to apply a force against the pusher 140 to cause the pusher 140 to urge the cartridge unit 70 against the stop 135 at a time just prior to when the label is applied to (tagged to) the cartridge unit 70 and to maintain this force during the time period while the label is applied to the cartridge unit 70. The swash plate 50 may further be configured to not apply the force to the pusher 140 when the cartridge unit 70 is being received in the seat 115 (e.g., prior to tagging) and also when the cartridge unit 70 is being moved out of the seat 115 to another drum (e.g., after tagging).

Figure 6:
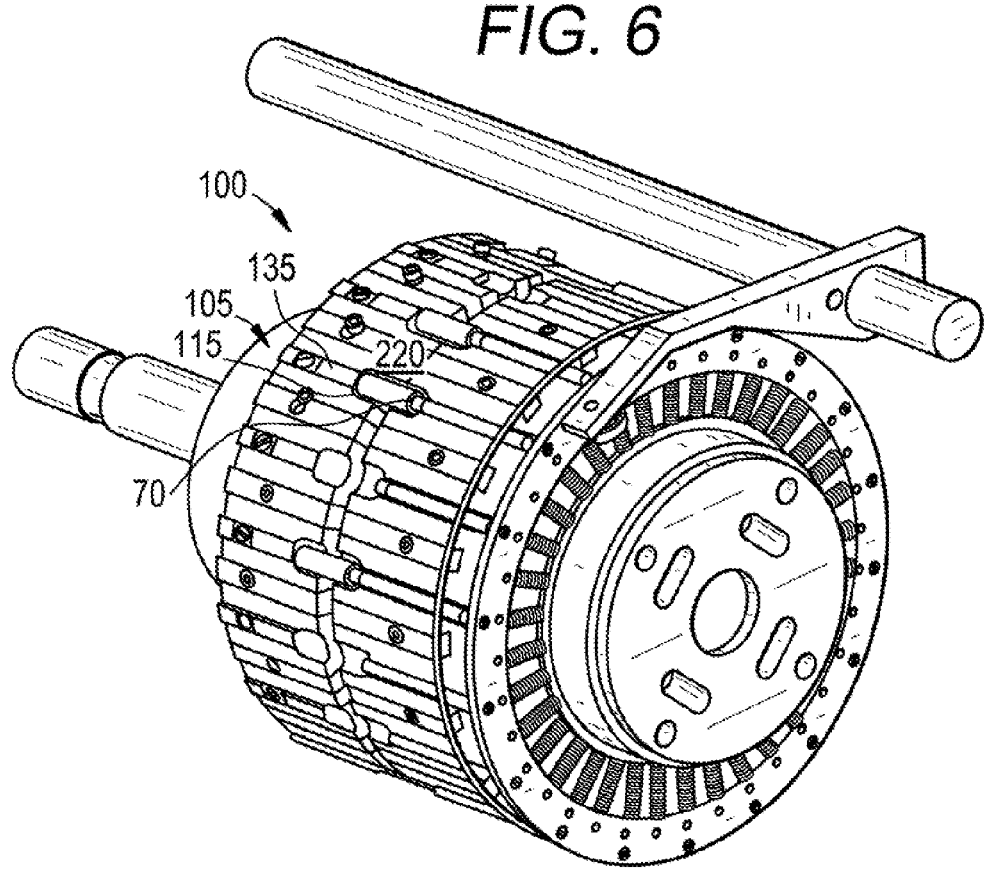
FIGS. 6 and 7a show aspects of applying a label to an electronic vapor device in accordance with an example embodiment.
Figure 7A:
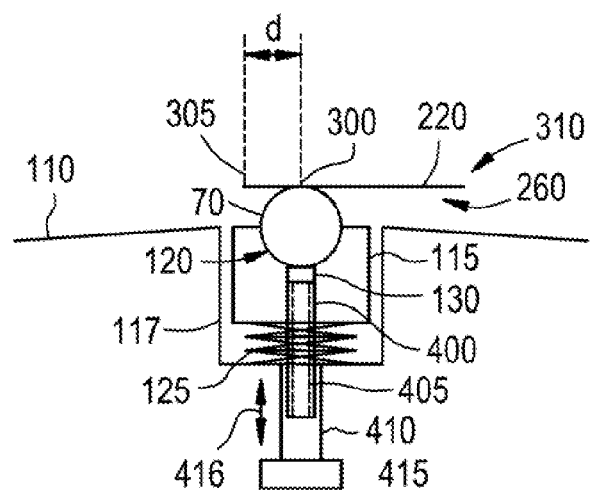

FIGS. 6 and 7a show aspects of applying a label 220 to a casing 6 of a cartridge unit 70 in accordance with an example embodiment. As shown in FIGS. 6 and 7a, a cartridge unit 70 is held in a seat 115 in drum 100 when the tagging drum 215 brings the first side 260 (e.g., the adhesive side) of the label 220 into contact with the exterior surface of the cartridge unit 70, e.g., at location 225 of FIG. 3. In example embodiments, the rotation of the tagging drum 215 and the drum 100 are controlled such that an intermediate portion 300 of the label 220 contacts the cartridge unit 70. More specifically, in an example embodiment, the intermediate portion 300 is between the leading edge 305 of the label 220 and the trailing edge 310 of the label 220, and closer to the leading edge 305 than the trailing edge 310.

As shown in FIG. 7a, the contact location at the intermediate portion 300 is a length "d" away from the leading edge 305. In an example embodiment, the length "d" is about 1 mm, although other lengths may be used. Making the contact point at an intermediate location 300 instead of the leading edge 305 yields improved tagging and rolling of the label 220 on the relatively hard and unyielding outer surface of the cartridge unit 70 (that is constructed, for example, of aluminum alloy) as compared to a tagging operation on a conventional article that has a relatively soft outer surface (that is constructed, for example, of paper, filter material, or the like) that yields at the locus of application during the tagging process.

With continued reference to FIG. 7a, the seat 115 may include or be connected to a post 400 having an internal channel 405. A first end of the channel 405 communicates with the hole 130 for providing vacuum force at the seat. A second end of the channel 405, opposite the first end, communicates with another channel 410 that is formed in the drum 100 and which is in communication with a vacuum source 415 associated with the drum 100. In this manner, the vacuum source 415 associated with the drum 100 may be used to selectively apply vacuum force at the seat via the channel 405 and hole 130. In an example implementation, the post 400 and channel 405 are embodied as a hollow cylindrical tube, although any suitable shape may be used.

In example embodiments, the post 400 is configured to be axially moveable inside the channel 410 as indicated by arrow 416. The post 400 may be sized relative to the channel 410 such that the lower end of the post 400 remains the channel 410 through the entire range of motion of the seat 115. In this manner, vacuum may be maintained at the seat 115 when the seat 115 moves axially against the spring 125.

In aspects, the post 400 may be located inside the spring 125. For example, the spring 125 may have the shape of a helical spring, and the post 400 may be centrally located within the spring and substantially coaxial with a longitudinal axis of the spring. More than one post 400 and spring 125 may be used for each seat 155. For example, as shown in FIG. 5, each seat 115 may be associated with two springs 125 and posts 400.

Figure 7B:
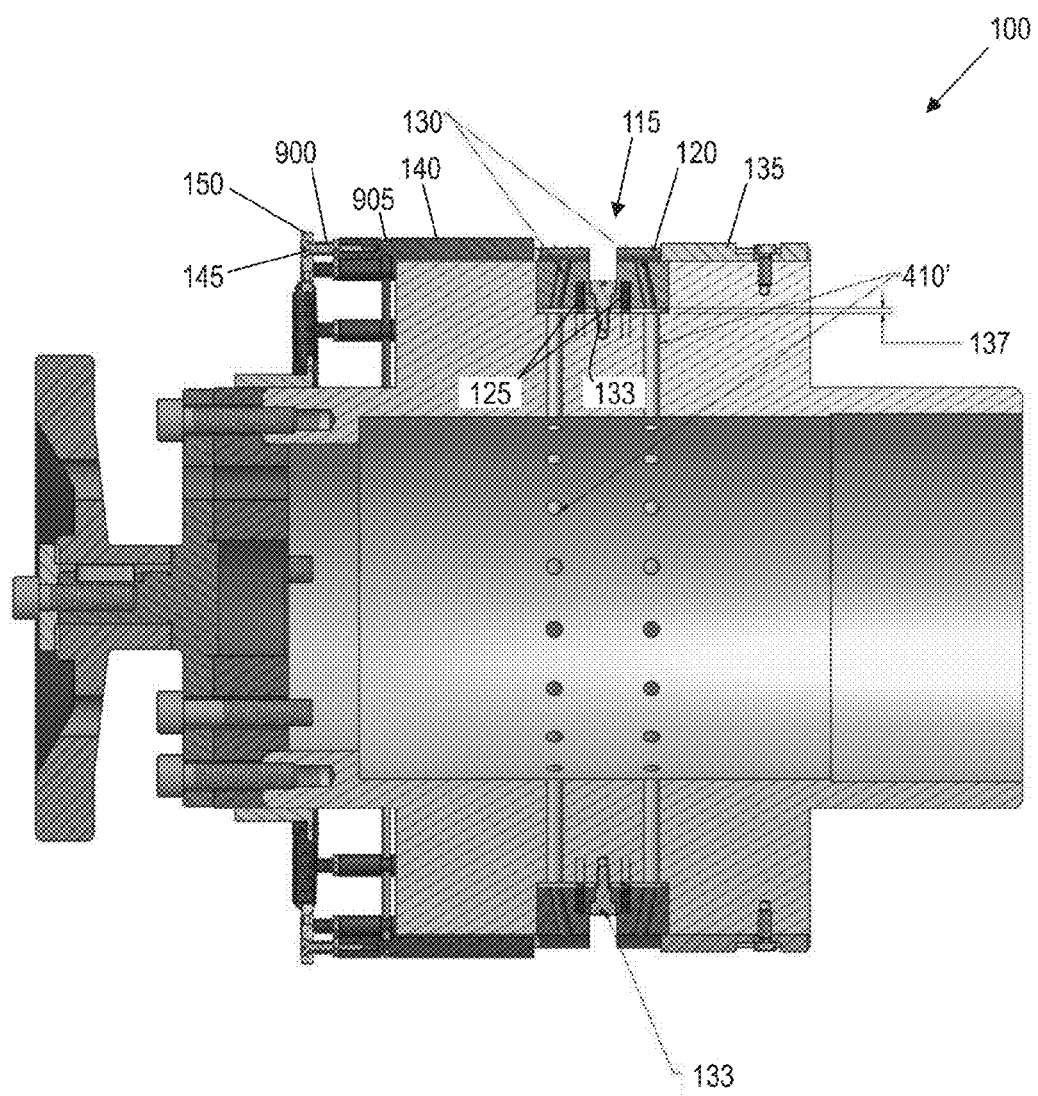
FIGS. 7b, 8, and 9 show aspects of drums in accordance with an example embodiment.

FIG. 7b shows a cross section of an example implementation of drum 100 of FIG. 4. As shown in FIG. 7b, the drum 100 includes a seat 115 with a seat groove 120 that is sized to hold a cartridge unit 70. As described herein, a swash plate 150 and a pusher 140 may be arranged to selectively push a cartridge unit 70 against the stop 135 during a label tagging process. In example embodiments, a screw 145 is threaded into the end of the pusher 140, with the screw 145 extending through a hole in the swash plate 150 without being threadedly engaged to the swash plate 150. In aspects, a spring 900 surrounds the screw 145 and contacts the pusher 140 and the swash plate 150. In operation, a cam follower or similar mechanism pushes a portion of the swash plate 150 inward, which applies an axial force to the spring 900 and the pusher 140 that, in turn, exerts an axial force on a cartridge unit 70 in the seat 115. The components of the system may be structured and arranged such that the axial force applied against the cartridge unit 70 in this manner is sufficient to hold the cartridge unit 70 against the stop 135 and prevent the cartridge unit 70 from rotating in the seat 115 when the label is applied to the cartridge unit 70. The spring 900 advantageously prevents binding during this pushing operation so that the pusher 140 will not damage the cartridge unit 70 during the pushing. In example embodiments, one or more circumferential springs 905 may be arranged around the pushers 140 to prevent the pushers 140 from pivoting out of the respective flutes of the drum.

With continued reference to FIG. 7b, the limit stop structure 133 may comprise a shoulder bolt or the like. A position of the shoulder bolt may be adjusted, e.g., by screwing the bolt further in or further out of the body of the drum 100, to adjust an outer limit of travel (e.g., translational motion) of the seat 115 relative to the body of the drum 100. The extent of travel 137 of the seat 115 relative to the body 100 of the drum may be set to any desired value, such as 1.5 mm or similar.

As described herein, the seat 115 may include vacuum holes 130 that are in communication with a vacuum source in the body of the drum 100. As shown in FIG. 7b, the vacuum holes 130 may be offset from (e.g., not coincident) with the springs 125. The vacuum holes 130 may be in communication with vacuum holes 410' in the body of the drum 100 and thus used to selectively apply vacuum force at the seat groove 120 for retaining a cartridge unit 70 in the seat groove 120.

Figure 8:
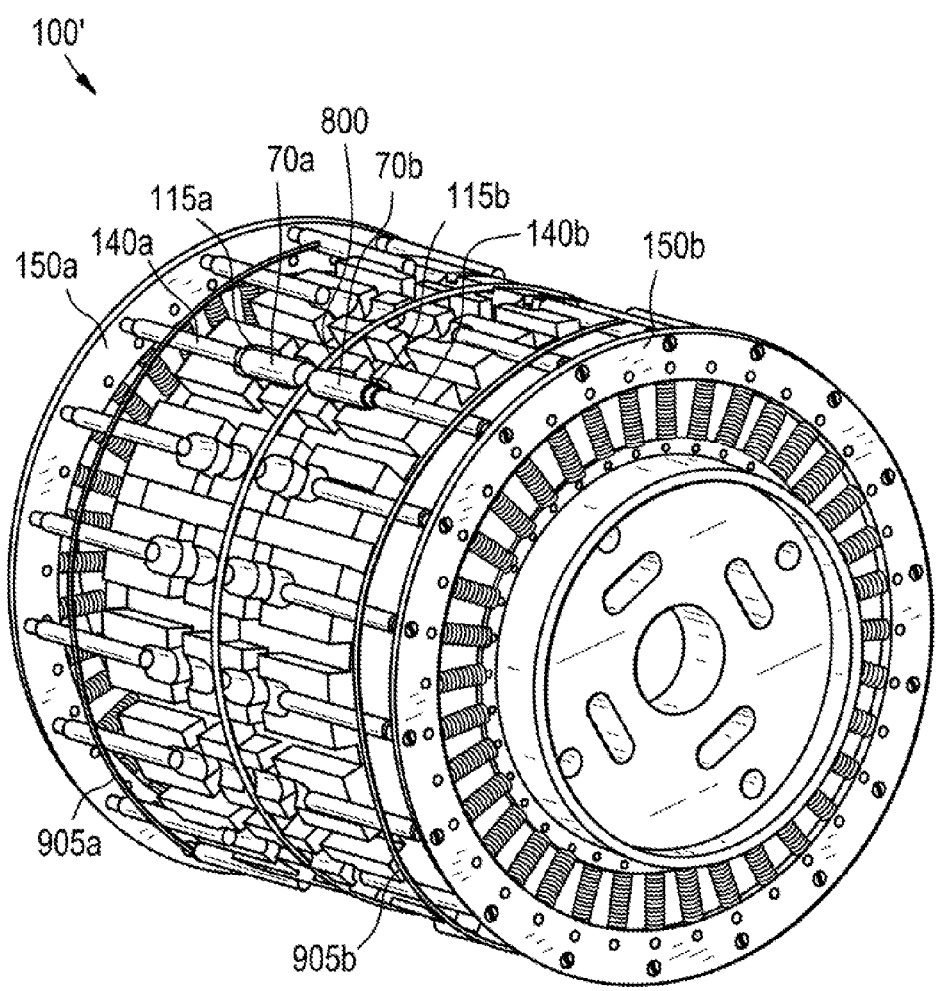

FIG. 8 shows aspects of another drum 100' in accordance with an example embodiment. Drum 100' is similar to drum 100 in that it includes a cylindrical body with a plurality of grooves spaced apart across its roll face. The drum 100', including the roll face and the interior surfaces of the grooves, is composed of a metal or metal alloy, such as steel. The drum 100 described with respect to FIGS. 4 and 5 includes a single seat 115 centered in each groove. The drum 100' shown in FIG. 8 includes two seats 115a and 115b in each groove. In example embodiments, the seats 115a and 115b are located in pockets of the groove, and each seat 115a and 115b includes a seat groove that is sized and shaped to hold a cartridge unit 70a-b. In this manner, each flute 105 may hold two cartridge units 70a-b instead of one. Accordingly, using the drum 100' in system 200 provides the ability to produce twice as many labeled cartridge units when operating at a same speed as with drum 100, or to produce a same amount of labeled cartridge units when operating at half the speed as with drum 100.

Still referring to FIG. 8, the drum 100' includes a stop 800 between the two seats 115a and 115b. In aspects, a first pusher 140a is adjacent to the seat 115a in the groove and is selectively moveable inward toward the stop 800. Similarly, a second pusher 140b is adjacent the seat 115b in the groove and is selectively moveable inward toward the stop 800. In example embodiments, the pushers 140a and 140b are configured with swash plates 150a-b to selectively apply an axial force to the respective cartridge units 70a-b that pushes the respective cartridge units 70a-b against the stop 800 to hold the cartridge units 70a-b snug, e.g., when a label 220 is being tagged to each cartridge unit 70a-b. The swash plates 150a-b may operate in a manner similar to swash plate 150 described with respect to FIG. 4. The swash plates 150a-b, pushers 140a-b, and stop 800 may be structured and arranged to align the cartridge units 70a-b with respective labels at the time of tagging the labels to the cartridge units, e.g., in a manner similar to that described with respect to FIG. 4. The drum 100' may also include respective circumferential springs 905a and 905b.

Figure 9:
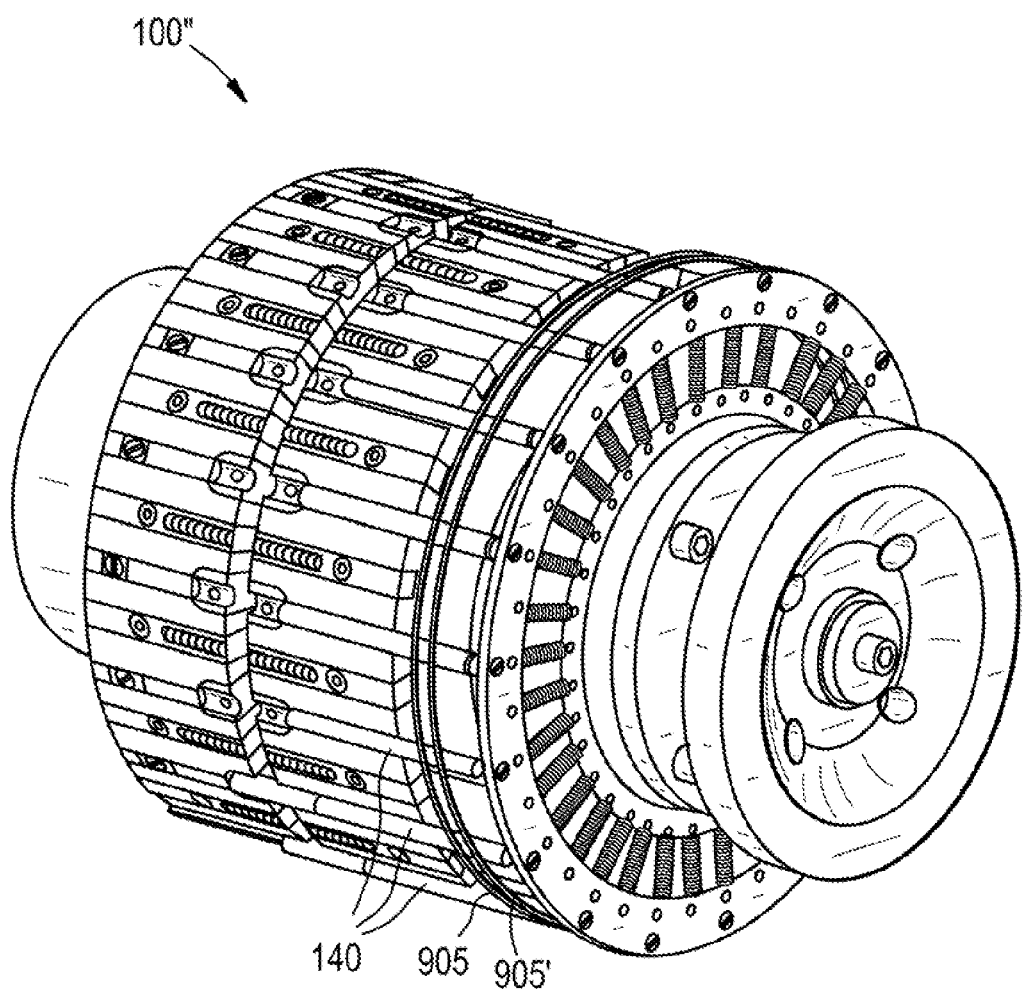

FIG. 9 shows a drum 100" in accordance with aspects herein. The drum 100" is similar to drum 100 of FIG. 4, and includes two circumferential springs 905 and 905' surrounding the pushers 140.

The particulars shown herein are by way of example and for purposes of illustrative discussion only and are presented in the cause of providing what is believed to be the most useful and readily understood description of the principles and conceptual aspects. In this regard, no attempt is made to show structural details in more detail than is necessary for fundamental understanding, the description taken with the drawings making apparent to those skilled in the art how the several forms disclosed herein may be embodied in practice.

It is noted that the foregoing examples have been provided merely for the purpose of explanation and are in no way to be construed as limiting. While aspects have been described with reference to example embodiments, it is understood that the words which have been used herein are words of description and illustration, rather than words of limitation. Changes may be made, within the purview of the appended claims, as presently stated and as amended, without departing from the scope and spirit of the present disclosure in its aspects. Although aspects have been described herein with reference to particular means, materials, and/or embodiments, the present disclosure is not intended to be limited to the particulars disclosed herein; rather, it extends to all functionally equivalent structures, methods and uses, such as are within the scope of the appended claims.

The invention claimed is:

1. A rotatable drum for automated manufacturing of e-vapor devices, comprising:
 a drum body including a roll face bounded by opposing end faces, the roll face defining a plurality of pockets therein; and
 a first seat structure tractably-mounted in each of the plurality of pockets of the drum body with a post and a resilient element, the first seat structure including a first outer surface and an opposing first inner surface, the first outer surface defining a first groove therein and facing outward from the drum body, the first groove configured to receive and hold a first casing of the e-vapor devices, the post extending through the resilient element and connected to the first inner surface of the first seat structure.

2. The rotatable drum of claim 1, wherein the first seat structure is composed of a plastic, and the first casing is composed of a metal or a metal alloy.

3. The rotatable drum of claim 2, wherein the plastic is polyoxymethylene, and the metal alloy is an aluminum alloy.

4. The rotatable drum of claim 1, wherein the resilient element is disposed between the first inner surface of the first seat structure and a base of a corresponding one of the plurality of pockets, the first seat structure being moveable along a radial direction of the drum body via the resilient element, the resilient element configured to bias the first seat structure outward from the drum body along the radial direction.

5. The rotatable drum of claim 1, further comprising:
 a pusher structure moveably arranged in each of the plurality of pockets, the pusher structure configured to apply a lateral force to a side of the first casing in the first groove of the first seat structure.

6. The rotatable drum of claim 5, further comprising:
 a spring oriented longitudinally in each of the plurality of pockets, the spring configured to bias the pusher structure toward the first seat structure.

7. The rotatable drum of claim 1, further comprising:
 a second seat structure tractably-mounted in each of the plurality of pockets of the drum body, the second seat structure including a second outer surface and an opposing second inner surface, the second outer surface defining a second groove therein and facing outward from the drum body, the second groove configured to receive and hold a second casing of the e-vapor devices.

8. The rotatable drum of claim 7, further comprising:
 a stop structure between the first seat structure and the second seat structure;
 a first pusher structure moveably arranged in each of the plurality of pockets, the first seat structure being between the first pusher structure and the stop structure; and
 a second pusher structure moveably arranged in each of the plurality of pockets, the second seat structure being between the stop structure and the second pusher structure.

9. The rotatable drum of claim 8, wherein:
 the first pusher structure is configured to apply a lateral force to a side of the first casing in the first groove of the first seat structure so as to push the first casing against the stop structure; and
 the second pusher structure is configured to apply a lateral force to a side of the second casing in the second groove of the second seat structure so as to push the second casing against the stop structure.

10. A system for automated manufacturing of e-vapor devices, comprising:
 a rotatable drum including
  a drum body including a roll face bounded by opposing end faces, the roll face defining a plurality of pockets therein, and
  a seat structure tractably-mounted in each of the plurality of pockets of the drum body, the seat structure including an outer surface and an opposing inner surface, the outer surface defining a groove therein and facing outward from the drum body, the groove configured to receive and hold a casing of the e-vapor devices;
 a tagging assembly configured to attach a label to the casing in the groove of the seat structure, the tagging assembly configured to initially attach a central portion of the label to an outer surface of the casing such that a leading edge and a trailing edge of the label do not contact the casing when the label is initially attached to the casing; and a wrapping assembly configured to wrap the label around the casing.

11. The system of claim 10, wherein the rotatable drum further includes a resilient element disposed between the inner surface of the seat structure and a base of a corresponding one of the plurality of pockets, the seat structure being moveable along a radial direction of the drum body via the resilient element, the resilient element configured to bias the seat structure outward from the drum body along the radial direction.

12. The system of claim 10, wherein the tagging assembly is configured to initially attach the central portion of the label to the outer surface of the casing such that the central portion is closer to the leading edge than the trailing edge.

13. The system of claim 10, wherein the tagging assembly is configured to remove a backing sheet from a continuous web to expose a pressure sensitive adhesive and to cut the label from the continuous web.

14. A method of automated manufacturing of e-vapor devices, comprising:
receiving and holding a casing of the e-vapor devices in a seat structure that is tractably-mounted in a pocket of a rotating drum;
tagging a label to the casing while the casing is held in the seat structure, the tagging including initially attaching a central portion of the label to an outer surface of the casing such that a leading edge and a trailing edge of the label do not contact the casing when the label is initially tagged to the casing; and
wrapping the label around the casing.

15. The method of claim 14, wherein:
the seat structure is moveable along a radial direction of the rotating drum; and
the seat structure is biased outward from the rotating drum along the radial direction.

16. The method of claim 14, further comprising:
removing a backing sheet from a continuous web to expose a pressure sensitive adhesive; and
cutting the label from the continuous web prior to the tagging.

17. The method of claim 14, further comprising:
inserting components corresponding to one of the e-vapor devices in the casing after the wrapping.

18. The rotatable drum of claim 1, wherein the resilient element is a helical structure wound around the post.

19. The rotatable drum of claim 1, wherein the post is centrally located within and substantially coaxial with a longitudinal axis of the resilient element.

* * * * *